(12) United States Patent
Hinz et al.

(10) Patent No.: US 10,544,455 B2
(45) Date of Patent: Jan. 28, 2020

(54) SEQUENCING METHODS, COMPOSITIONS AND SYSTEMS USING TERMINATOR NUCLEOTIDES

(71) Applicants: LIFE TECHNOLOGIES CORPORATION, Carlsbad, CA (US); LIFE TECHNOLOGIES GmbH, Darmstadt (DE)

(72) Inventors: Wolfgang Hinz, Killingworth, CT (US); Peter Vander Horn, Encinitas, CA (US); Earl Hubbell, Palo Alto, CA (US); Christian Woehler, Heidelberg (DE)

(73) Assignees: LIFE TECHNOLOGIES CORPORATION, Carlsbad, CA (US); LIFE TECHNOLOGIES GMBH, Darmstadt (DE)

( * ) Notice: Subject to any disclaimer, the term of this patent is extended or adjusted under 35 U.S.C. 154(b) by 423 days.

(21) Appl. No.: 14/856,220

(22) Filed: Sep. 16, 2015

(65) Prior Publication Data

US 2016/0097091 A1 Apr. 7, 2016

Related U.S. Application Data

(60) Provisional application No. 62/059,837, filed on Oct. 3, 2014.

(51) Int. Cl.
C12P 19/34 (2006.01)
C12Q 1/6869 (2018.01)

(52) U.S. Cl.
CPC .................................. *C12Q 1/6869* (2013.01)

(58) Field of Classification Search
None
See application file for complete search history.

(56) References Cited

U.S. PATENT DOCUMENTS

| | | | |
|---|---|---|---|
| 7,057,026 B2 | 6/2006 | Barnes et al. | |
| 7,566,537 B2 | 7/2009 | Balasubramanian et al. | |
| 7,635,578 B2 | 12/2009 | Ju et al. | |
| 7,713,698 B2 | 5/2010 | Ju et al. | |
| 7,785,796 B2 | 8/2010 | Balasubramanian et al. | |
| 7,790,869 B2 | 9/2010 | Ju et al. | |
| 7,883,869 B2 | 2/2011 | Ju et al. | |
| 7,888,015 B2* | 2/2011 | Toumazou | C12Q 1/6825 435/6.11 |
| 7,893,227 B2 | 2/2011 | Wu et al. | |
| 7,897,737 B2 | 3/2011 | Wu et al. | |
| 7,948,015 B2 | 5/2011 | Rothberg et al. | |
| 7,964,352 B2 | 6/2011 | Wu et al. | |
| 8,088,575 B2 | 1/2012 | Ju et al. | |
| 8,148,503 B2 | 4/2012 | Litosh et al. | |
| 8,158,346 B2 | 4/2012 | Balasubramanian et al. | |
| 8,198,029 B2 | 6/2012 | Wu et al. | |
| 8,361,727 B2 | 1/2013 | Wu et al. | |
| 8,497,360 B2 | 7/2013 | Litosh et al. | |
| 9,309,569 B2 | 4/2016 | Gordon et al. | |
| 9,617,590 B2 | 4/2017 | Edwards et al. | |
| 2003/0215862 A1 | 11/2003 | Parce et al. | |
| 2008/0032295 A1* | 2/2008 | Toumazou | C12Q 1/6825 435/6.11 |
| 2008/0166727 A1 | 7/2008 | Esfandyarpour et al. | |
| 2009/0026082 A1 | 1/2009 | Rothberg et al. | |
| 2009/0127589 A1 | 5/2009 | Rothberg et al. | |
| 2009/0203531 A1 | 8/2009 | Kurn | |
| 2010/0137143 A1 | 6/2010 | Rothberg et al. | |
| 2010/0197507 A1 | 8/2010 | Rothberg et al. | |
| 2010/0282617 A1 | 11/2010 | Rothberg et al. | |
| 2010/0300559 A1 | 12/2010 | Schultz et al. | |
| 2010/0300895 A1 | 12/2010 | Nobile et al. | |
| 2010/0301398 A1 | 12/2010 | Rothberg et al. | |
| 2012/0052489 A1 | 3/2012 | Gordon et al. | |
| 2014/0242579 A1* | 8/2014 | Zhou | C07H 19/10 435/6.11 |
| 2014/0329712 A1 | 11/2014 | Edwards et al. | |

(Continued)

FOREIGN PATENT DOCUMENTS

WO    WO-2016153999 A1    9/2016

OTHER PUBLICATIONS

Anderson, et al., "A system for multiplexed direct electrical detection of DNA synthesis", Sensors and Actuators B Chem., vol. 129, 2008, 79-86.

(Continued)

*Primary Examiner* — Kenneth R Horlick
(74) *Attorney, Agent, or Firm* — Life Technologies Corporation; Paula Schoeneck

(57) ABSTRACT

In some embodiments, the disclosure relates generally to methods, as well as compositions, systems, kits and apparatuses, for performing nucleotide incorporation, comprising: (a) providing a surface including one or more reaction sites containing a polymerase and a nucleic acid template that has, or is hybridized to, an extendible end; (b) performing a first nucleotide flow by contacting one or more of the reaction sites with a first solution including one or more types of terminator nucleotide; (c) incorporating at least one type of terminator nucleotide at the extendible end of the nucleic acid template contained within at least one of the reaction sites using the polymerase; and (d) detecting a non-optical signal indicating the nucleotide incorporation using a sensor that is attached or operatively linked to the at least one reaction site.

17 Claims, No Drawings

(56) References Cited

U.S. PATENT DOCUMENTS

2018/0119217 A1    5/2018   Hinz et al.

OTHER PUBLICATIONS

Pourmand, N. et al., "Direct electrical detection of DNA synthesis", PNAS, vol. 103(17), 2006, pp. 6466-6470.
Purushothaman, S. et al., "Towards Fast Solid State DNA Sequencing", IEEE ISCAS 2002 Proceedings, Circuits and Systems, vol. 4, 2002, pp. IV-169-IV-172.
Sakata, T. et al., "DNA Sequencing Based on Intrinsic Molecular Charges", Angewandte Chemie International Edition 2006, vol. 118, 2006, 2283-2286.
Sakurai, T. et al., "Real-Time Monitoring of DNA Polymerase Reactions by a Micro ISFET pH Sensor", Anal Chem, vol. 64(17), 1992, pp. 1996-1997.
PCT/US2016/023139 International Preliminary Report on Patentability dated Sep. 26, 2017.
PCT/US2016/023139, International Search Report and Written Opinion dated Jun. 16, 2016, 9 pages.

\* cited by examiner

SEQUENCING METHODS, COMPOSITIONS AND SYSTEMS USING TERMINATOR NUCLEOTIDES

This application claims the benefit of priority under 35 U.S.C. § 119 to U.S. Provisional Application No. 62/059,837, filed Oct. 3, 2014, the disclosure of which aforementioned application is incorporated by reference in its entirety.

Throughout this application various publications, patents, and/or patent applications are referenced. The disclosures of these publications, patents, and/or patent applications in their entireties are hereby incorporated by reference into this application in order to more fully describe the state of the art to which this invention pertains.

Nucleic acid sequencing, in which the order of nucleotides in a nucleic acid molecule is determined, has become ubiquitous in a wide variety of medical applications, such as biological research, genetic testing, and so forth. One type of sequencing utilized in such applications is sequencing-by-synthesis in which the order of nucleotides in a nucleic acid strand is determined by synthesizing a corresponding strand. Typically, the synthesized strand is complementary to the template strand and is synthesized in a template-dependent manner, wherein the order of addition of nucleotides is determined based on a particular base-pairing paradigm, e.g., Watson-Crick type base pairing. Current sequencing methods are also subject to technical constraints that add to the complexity of the sequencing reaction and ultimately limit the quality and/or amount of sequence information that can be derived from a biological sample. For example, several current sequencing systems use terminator nucleotides (also referred to herein as "chain terminating nucleotides") that, once incorporated into the end of a synthesized strand, inhibit or block outright further nucleotide incorporations at that end. All terminator-based sequencing chemistries described to date require the use of different fluorescent labels associated with different nucleotide types, and these labels must be spectrally resolved to identify each nucleotide incorporated serially into the synthesized strand. Such spectral resolution of fluorescent labels is imperfect because of the spectral overlap between the different fluorescent dyes employed, leading to systemic sequencing error. Examples of systems employing fluorescently labeled terminators include sequencing technology provided by Illumina, Inc. and Intelligent Bio-Systems, Inc. (Qiagen). Furthermore, the labels and the blocking moieties must both be removed via cleavage reactions prior to incorporation of the subsequent nucleotide, and the performance of the sequencing reaction as a whole is therefore limited by the cleavage efficiency. The presence of a small proportion of uncleaved products perpetuates in the sequencing reaction, leading to loss of phase and spectral cross-contamination of signals, ultimately limiting the sequencing read length and/or total sequencing throughput.

Some other systems have aimed to avoid such problems by incorporating methods that avoid the need for fluorescent labels or terminator groups; examples including the semiconductor-based PGM™ and Proton™ sequencers developed by Ion Torrent™ Systems, Inc. (Thermo Fisher Scientific). Such systems operate by using semiconductors to detect a non-optical signal indicating the nucleotide incorporation. In certain limited contexts, however, the accuracy of such systems may be limited by the ability of the system to accurately quantify the nucleotide incorporation signal, particularly in the context of sequencing homopolymeric regions (i.e., nucleic acid regions consisting of two or more identical contiguous nucleotides). As the length of the homopolymeric region increases, the ability of the system to accurately quantify the number of identical nucleotides within the homopolymeric region may reduce, particularly when the length of the homopolymer exceeds five, six, seven, ten or twelve nucleotides.

SUMMARY

In some embodiments, the disclosure relates generally to methods, as well as compositions, systems, kits and apparatuses, for performing nucleotide incorporation.

In some embodiments, the disclosed methods (and related compositions, systems, kits and apparatuses) for performing nucleotide incorporation include or otherwise involve use of a surface.

In some embodiments, the surface includes one or more reaction sites.

Optionally, at least one reaction site contains a sensor.

Optionally, at least on reaction site is attached or is operably linked to a sensor.

Optionally, at least one reaction site contains one or more polymerases.

In some embodiments, at least one reaction site further includes one or more nucleic acid templates (e.g., template polynucleotides). The nucleic acid template can be single strand or double stranded.

In some embodiments, the nucleic acid template contains, or is hybridized to, an extendible end. The extendible end can serve as the site for incorporation of additional nucleotides into the extendible end. The incorporation can be catalyzed by a polymerase.

In some embodiments, the nucleic acid template is at least partially double stranded and the extendible end includes a nick or gap within a double stranded region of the nucleic acid template.

In some embodiments, the nucleic acid template is at least partially single stranded, and the extendible end is part of a second nucleic acid molecule (e.g., an oligonucleotide primer or a template or other complementary strand) that is hybridized to the nucleic acid template. Typically, the second nucleic acid molecule is hybridized to a portion of the nucleic acid template that is immediately adjacent to a single stranded region of the nucleic acid template.

Optionally, the extendible end includes a free hydroxyl group on the sugar ring of a terminal nucleotide. The hydroxyl group can serve as the site for incorporation of additional nucleotides into the extendible end. The incorporation can be catalyzed by a polymerase.

Optionally, the nucleic acid is hybridized to an oligonucleotide primer having an extendible end.

In some embodiments, the nucleic acid template has an extendible end.

In some embodiments, methods for incorporating a nucleotide comprises providing a surface which includes one or more reaction sites, the reaction sites containing at least one polymerase and one or more nucleic acid templates.

In some embodiments, the disclosed methods (and related compositions, systems, kits and apparatuses) for performing nucleotide incorporation include or otherwise involve performing a first nucleotide flow.

Optionally, the first nucleotide flow can be performed by contacting one or more of the reaction sites with a first solution.

Optionally, the first solution contains one or more nucleotides, where the nucleotides contact the polymerases and/or the nucleic acid templates at the reaction sites.

In some embodiments, the first solution includes one or more terminator nucleotides.

Optionally, the first solution includes a single type or a plurality of different types of terminator nucleotides.

In some embodiments, the first solution includes any one or any combination of adenosine, guanosine, cytosine, thymidine and/or uridine terminator nucleotides.

In some embodiments, the disclosed methods (and related compositions, systems, kits and apparatuses) for performing nucleotide incorporation include or otherwise involve incorporating at least one terminator nucleotide into the nucleic acid template.

Optionally, at least one reaction site includes one or more polymerases that incorporates at least one terminator nucleotide into the nucleic acid template Optionally, the polymerase at the reaction site incorporates at least one terminator nucleotide at the extendible end of the nucleic acid template.

In some embodiments, the disclosed methods (and related compositions, systems, kits and apparatuses) for performing nucleotide incorporation include or otherwise involve detecting nucleotide incorporation.

In some embodiments, detecting nucleotide incorporation includes detecting a non-optical signal that indicates that nucleotide incorporation has occurred.

Optionally, the nucleotide incorporation is detected using a sensor.

Optionally, the sensor is attached or operatively linked to at least one reaction sites.

Optionally, the sensor detects the non-optical signal that is associated with the nucleotide incorporation.

In some embodiments, the disclosed methods (and related compositions, systems, kits and apparatuses) for performing nucleotide incorporation include or otherwise involve analyzing the non-optical signal.

In some embodiments, the disclosed methods (and related compositions, systems, kits and apparatuses) for performing nucleotide incorporation include or otherwise involve identifying the incorporated nucleotide.

In some embodiments, the nucleotide that is incorporated includes adenosine, guanosine, cytosine, thymidine or uridine.

In some embodiments, the disclosed methods (and related compositions, systems, kits and apparatuses) for performing nucleotide incorporation include or otherwise involve deblocking the terminator nucleotides that were included in the first nucleotide flow.

Optionally, the deblocking step includes removing the terminator moiety from the terminator nucleotide.

In some embodiments, the disclosed methods (and related compositions, systems, kits and apparatuses) for performing nucleotide incorporation include or otherwise involve performing a second nucleotide flow.

Optionally, the second nucleotide flow can be performed by contacting one or more of the reaction sites with a second solution.

Optionally, the second solution contains one or more nucleotides, where the nucleotides contact the polymerases and/or the nucleic acid templates at the reaction sites.

Optionally, the second solution includes a single type or a plurality of different types of terminator nucleotides.

Optionally, the second solution includes one or more types of terminator nucleotides.

In some embodiments, the second solution includes any one or any combination of adenosine, guanosine, cytosine, thymidine and/or uridine terminator nucleotides.

Optionally, the second solution includes at least one non-terminator nucleotide.

In some embodiments, the second solution includes a single type or a plurality of different types of non-terminator nucleotides.

In some embodiments, the disclosed methods (and related compositions, systems, kits and apparatuses) for performing nucleotide incorporation include or otherwise involve performing a first series of nucleotide flows.

Optionally, the first series of nucleotide flows comprises two or more nucleotide flows.

Optionally, each nucleotide flow in the first series of nucleotide flows includes contacting one or more reaction sites with a solution of nucleotides.

Optionally, the solution of nucleotides, in the first series of nucleotide flows, contains one or more nucleotide types.

In some embodiments, the disclosed methods (and related compositions, systems, kits and apparatuses) for performing nucleotide incorporation include or otherwise involve detecting nucleotide incorporation.

In some embodiments, the nucleotide incorporation occurs at the one or more reaction sites.

In some embodiments, the disclosed methods (and related compositions, systems, kits and apparatuses) for performing nucleotide incorporation include or otherwise involve detecting a lack of nucleotide incorporation.

The lack of nucleotide incorporation can be detected at the one or more reaction sites.

Optionally, the detecting step is performed after each nucleotide flow in a first series of nucleotide flows.

Optionally, the detecting step is performed prior to a subsequent nucleotide flow in the first series of nucleotide flows.

Optionally, the detecting step is performed after a first nucleotide flow in the first series of nucleotide flows.

Optionally, the detecting step is performed after a second nucleotide flow in the first series of nucleotide flows.

Optionally, the detecting step is performed prior to the second nucleotide flow in the first series of nucleotide flows.

In some embodiments, the disclosed methods (and related compositions, systems, kits and apparatuses) for performing nucleotide incorporation include or otherwise involve performing a second series of nucleotide flows.

Optionally, the second series of nucleotide flows comprises two or more nucleotide flows.

Optionally, each nucleotide flow in the second series of nucleotide flows includes contacting one or more reaction sites with a solution of nucleotides.

Optionally, the solution of nucleotides contains one or more nucleotide types.

In some embodiments, the solution of nucleotides includes one or more terminator nucleotides. The one or more terminator nucleotides optionally include a reversible terminator nucleotide.

In some embodiments, a reversible terminator nucleotide comprises a nucleotide linked to a blocking moiety, where the blocking moiety is linked to any portion of the base, sugar or any phosphate group, and the blocking moiety is removable.

In some embodiments, the disclosed methods (and related compositions, systems, kits and apparatuses) for performing nucleotide incorporation include or otherwise involve use of a sensor. The sensor is optionally configured to detect nucleotide incorporation. In some embodiments, the sensor comprises an ISFET.

In some embodiments, methods for nucleotide incorporation include terminator nucleotides which comprise dideoxy nucleotide.

In some embodiments, methods for nucleotide incorporation include terminator nucleotides which comprise reversible terminator nucleotides.

Optionally, a reversible terminator nucleotide comprises a nucleotide linked to a blocking moiety, where the blocking moiety is linked to any portion of the base or sugar, or linked to any phosphate group, and the blocking moiety is removable.

Optionally, the terminator nucleotides do not include a detectable moiety.

Optionally, the terminator nucleotides do not include an optically-detectable moiety.

Optionally, the terminator nucleotides do not include a fluorescent label or a luminescent label.

In some embodiments, the incorporated nucleotides that are identified include adenosine, guanosine, cytosine, thymidine or uridine.

In some embodiments, methods for incorporating nucleotides further comprise deblocking the terminator nucleotides that were incorporated, where the incorporated terminator nucleotides were included in the first nucleotide flow.

Optionally, the first series of nucleotide flows includes at least a first flow and a second flow.

Optionally, the first nucleotide flow, in the first series of nucleotide flows, can be performed by contacting one or more of the reaction sites with a first solution.

Optionally, the first solution, in the first series of nucleotide flows, contains one or more nucleotides, where the nucleotides contact the polymerases and/or the nucleic acid templates at the reaction sites.

In some embodiments, the first solution, in the first series of nucleotide flows, includes one or more terminator nucleotides.

Optionally, the first solution, in the first series of nucleotide flows, includes a single type or a plurality of different types of terminator nucleotides.

Optionally, the second nucleotide flow, in the first series of nucleotide flows, can be performed by contacting one or more of the reaction sites with a second solution.

Optionally, the second solution, in the first series of nucleotide flows, contains one or more nucleotides, where the nucleotides contact the polymerases and/or the nucleic acid templates at the reaction sites.

In some embodiments, the second solution, in the first series of nucleotide flows, includes one or more terminator nucleotides.

Optionally, the second solution, in the first series of nucleotide flows, includes a single type or a plurality of different types of terminator nucleotides.

In some embodiments, methods for nucleotide incorporation further comprise detecting nucleotide incorporation after each nucleotide flow in the first series of nucleotide flows.

In some embodiments, methods for nucleotide incorporation further comprise detecting nucleotide incorporation prior to a subsequent nucleotide flow in the first series of nucleotide flows.

In some embodiments, methods for nucleotide incorporation further comprise detecting nucleotide incorporation from a first series of nucleotide flows, wherein the nucleotide incorporation occurs at the one or more reaction sites.

In some embodiments, methods for nucleotide incorporation further comprise detecting a lack of nucleotide incorporation from a first series of nucleotide flows.

In some embodiments, methods for nucleotide incorporation further comprise determining the identity of the nucleotides incorporated following each nucleotide flow in the first series of nucleotide flows.

Optionally, the methods for nucleotide incorporation further comprise determining the identity of the nucleotides incorporated following at least the first and the second nucleotide flows in the first series of nucleotide flows.

Optionally, the nucleotides that are incorporated following at least the first and the second nucleotide flows in the first series of nucleotide flows include adenosine, guanosine, cytosine, thymidine or uridine.

In some embodiments, methods for nucleotide incorporation further comprise determining the number of nucleotides incorporated following each nucleotide flow in the first series of nucleotide flows.

Optionally, the methods for nucleotide incorporation further comprise determining the number of nucleotides incorporated following at least the first and the second nucleotide flows in the first series of nucleotide flows.

In some embodiments, the methods for nucleotide incorporation further comprise removing the extendible end from the nucleic acid template.

Optionally, the extendible end is removed from the nucleic acid template by denaturation.

Optionally, the extendible end is removed from the nucleic acid template with heat or alkaline conditions.

Optionally, the extendible end is removed from the nucleic acid template after completing the first series of nucleotide flows.

Optionally, the extendible end is removed from the nucleic acid template prior to commencing the second series of nucleotide flows.

In some embodiments, at least one flow, in the first series of nucleotide flows, contains at least one terminator nucleotide.

Optionally, at least one flow, in the first series of nucleotide flows, contains at least one non-terminator nucleotides.

Optionally, at least one flow, in the first series of nucleotide flows, contains only terminator nucleotides.

Optionally, at least one flow, in the first series of nucleotide flows, contains only non-terminator nucleotides.

Optionally, at least one flow, in the first series of nucleotide flows, contains at least one terminator nucleotide and at least one non-terminator nucleotide.

Optionally, at least the first flow, in the first series of nucleotide flows, contains at least one terminator nucleotide.

Optionally, at least the second flow, in the first series of nucleotide flows, contains at least one terminator nucleotide.

Optionally, all the flows, in the first series of nucleotide flows, contain only one or more types of terminator nucleotides.

Optionally, all the flows, in the first series of nucleotide flows, lack any non-terminator nucleotides.

Optionally, all the flows, in the first series of nucleotide flows, contain only one or more types of non-terminator nucleotides.

Optionally, the second series of nucleotide flows includes at least a first flow and a second flow.

Optionally, the first nucleotide flow, in the second series of nucleotide flows, can be performed by contacting one or more of the reaction sites with a first solution.

Optionally, the first solution, in the second series of nucleotide flows, contains one or more nucleotides, where the nucleotides contact the polymerases and/or the nucleic acid templates at the reaction sites.

In some embodiments, the first solution, in the second series of nucleotide flows, includes one or more terminator nucleotides.

Optionally, the first solution, in the second series of nucleotide flows, includes a single type or a plurality of different types of terminator nucleotides.

Optionally, the second nucleotide flow, in the second series of nucleotide flows, can be performed by contacting one or more of the reaction sites with a second solution.

Optionally, the second solution, in the second series of nucleotide flows, contains one or more nucleotides, where the nucleotides contact the polymerases and/or the nucleic acid templates at the reaction sites.

In some embodiments, the second solution, in the second series of nucleotide flows, includes one or more terminator nucleotides.

Optionally, the second solution, in the second series of nucleotide flows, includes a single type or a plurality of different types of terminator nucleotides.

In some embodiments, methods for nucleotide incorporation further comprise detecting nucleotide incorporation after each nucleotide flow in the second series of nucleotide flows.

In some embodiments, methods for nucleotide incorporation further comprise detecting nucleotide incorporation prior to a subsequent nucleotide flow in the second series of nucleotide flows.

In some embodiments, methods for nucleotide incorporation further comprise detecting nucleotide incorporation from a second series of nucleotide flows, wherein the nucleotide incorporation occurs at the one or more reaction sites.

In some embodiments, methods for nucleotide incorporation further comprise detecting a lack of nucleotide incorporation from a second series of nucleotide flows.

In some embodiments, methods for nucleotide incorporation further comprise determining the identity of the nucleotides incorporated following each nucleotide flow in the second series of nucleotide flows.

Optionally, the methods for nucleotide incorporation further comprise determining the identity of the nucleotides incorporated following at least the first and the second nucleotide flows in the second series of nucleotide flows.

Optionally, the nucleotides that are incorporated following at least the first and the second nucleotide flows in the second series of nucleotide flows include adenosine, guanosine, cytosine, thymidine or uridine.

In some embodiments, methods for nucleotide incorporation further comprise determining the number of nucleotides incorporated following each nucleotide flow in the second series of nucleotide flows.

Optionally, the methods for nucleotide incorporation further comprise determining the number of nucleotides incorporated following at least the first and the second nucleotide flows in the second series of nucleotide flows.

In some embodiments, the methods for nucleotide incorporation further comprise removing the extendible end from the nucleic acid template.

Optionally, the extendible end is removed from the nucleic acid template by denaturation.

Optionally, the extendible end is removed from the nucleic acid template with heat or alkaline conditions.

Optionally, the extendible end is removed from the nucleic acid template after completing the second series of nucleotide flows.

Optionally, the extendible end is removed from the nucleic acid template prior to commencing a subsequent series of nucleotide flows.

In some embodiments, at least one flow, in the second series of nucleotide flows, contains at least one terminator nucleotide.

Optionally, at least one flow, in the second series of nucleotide flows, contains at least one non-terminator nucleotides.

Optionally, at least one flow, in the second series of nucleotide flows, contains only terminator nucleotides.

Optionally, at least one flow, in the second series of nucleotide flows, contains only non-terminator nucleotides.

Optionally, at least one flow, in the second series of nucleotide flows, contains at least one terminator nucleotide and at least one non-terminator nucleotide.

Optionally, at least the first flow, in the second series of nucleotide flows, contains at least one terminator nucleotide.

Optionally, at least the second flow, in the second series of nucleotide flows, contains at least one terminator nucleotide.

Optionally, all the flows, in the second series of nucleotide flows, contain only one or more types of terminator nucleotides.

Optionally, all the flows, in the second series of nucleotide flows, lack any non-terminator nucleotides.

Optionally, all the flows, in the second series of nucleotide flows, contain only one or more types of non-terminator nucleotides.

In some embodiments, the first series of nucleotide flows consists only of flows containing at least one terminator nucleotide, and the second series of nucleotide flows consists only of flows containing at least one non-terminator nucleotide.

In some embodiments, the first series of nucleotide flows consists only of flows containing at least one non-terminator nucleotide, and the second series of nucleotide flows consists only of flows containing at least one terminator nucleotide.

In some embodiments, the disclosure relates generally to methods, as well as compositions, systems, kits and apparatuses, for performing nucleotide incorporation, comprising: (a) providing a surface including one or more reaction sites containing a polymerase and a nucleic acid template that has, or is hybridized to, an extendible end; (b) performing a first nucleotide flow by contacting one or more of the reaction sites with a first solution including one or more types of terminator nucleotide; (c) incorporating at least one type of terminator nucleotide at the extendible end of the nucleic acid template contained within at least one of the reaction sites using the polymerase; and (d) detecting a non-optical signal indicating the nucleotide incorporation using a sensor that is attached or operatively linked to the at least one reaction site.

In some embodiments, the methods further comprise analyzing the non-optical signal.

In some embodiments, the methods further comprise identifying the incorporated nucleotide.

In some embodiments, the methods further comprise deblocking the terminator nucleotide. Optionally, the deblocking includes removing the terminator moiety from the terminator nucleotide.

In some embodiments, the methods further comprise performing a second nucleotide flow by contacting at least some of the reaction sites with a second solution containing one or more types of nucleotide. Optionally, the first and/or the second flow solutions include only a single type of nucleotide. Optionally, the second flow solution includes a non-terminator nucleotide. Optionally, the second solution includes a terminator nucleotide.

In some embodiments, the methods further comprise performing a first series of nucleotide flows, each nucleotide flow in the first series including contacting one or more of the reaction sites with a solution including one or more nucleotide types.

In some embodiments, after each nucleotide flow in the first series and prior to the next flow, detecting nucleotide incorporation (or lack thereof) occurring at the one or more reaction sites.

In some embodiments, the methods further comprise determining the identity and number of nucleotides incorporated following each nucleotide flow in the first series.

In some embodiments, the methods further comprise performing a second series of nucleotide flows, each nucleotide flow in the second series including contacting one or more of the reaction sites with a solution including one or more nucleotide types.

In some embodiments, after each nucleotide flow in the second series and prior to the next flow, detecting nucleotide incorporation (or lack thereof) occurring at the one or more reaction sites.

In some embodiments, the methods further comprise determining the identity and number of nucleotides incorporated following each nucleotide flow in the second series.

In some embodiments, the methods further comprise denaturing or otherwise removing the extendible end from the nucleic acid template after completing the first series and prior to commencing the second series.

In some embodiments, the first series of nucleotide flows includes at least one flow containing a terminator nucleotide.

In some embodiments, the second series of nucleotide flows includes at least one flow containing a terminator nucleotide.

In some embodiments, the second series of nucleotide flows includes at least one flow containing a non-terminator nucleotide.

Optionally, the first series consists only of flows containing a terminator nucleotide.

Optionally, the second series consists only of flows containing a terminator nucleotide.

Optionally, the first series consists only of flows containing a non-terminator nucleotide.

Optionally, the second series consists only of flows containing a non-terminator nucleotide.

Optionally, the first series of nucleotide flows includes at least one flow containing a non-terminator nucleotide.

Optionally, the second series of nucleotide flows includes at least one flow containing a terminator nucleotide.

Optionally, the second series of nucleotide flows includes at least one flow containing a non-terminator nucleotide.

In some embodiments, the first series consists only of flows containing a terminator nucleotide and the second series consists only of flows containing a non-terminator nucleotide.

In some embodiments, the first series consists only of flows containing a non-terminator nucleotide and the second series consists only of flows containing a terminator nucleotide.

In some embodiments, the methods further comprise identifying the nucleotide with an error rate of less than 0.1%.

In some embodiments, the methods further comprise identifying the nucleotide with an error rate of less than 0.001%.

In some embodiments, the methods further comprise identifying the nucleotide in each of a series of nucleotide flows according to any method of the present teachings.

In some embodiments, the methods further comprise identifying the nucleotide with an error rate of less than 0.1%.

In some embodiments, the methods further comprise identifying the nucleotide with an error rate of less than 0.001%.

In some embodiments, the error rate includes a mismatch error rate of less than 0.001%, optionally less than 0.0001%.

In some embodiments, the error rate includes an in/del error rate of less than 0.1%, optionally less than 0.01%.

In some embodiments, the methods comprise identifying a series of contiguous nucleotides according to any of the methods of the present teachings.

In some embodiments, the methods further comprise identifying the nucleotide with an error rate of less than 0.1%.

In some embodiments, the methods further comprise identifying the nucleotide with an error rate of less than 0.001%.

In some embodiments, the error rate includes a mismatch error rate of less than 0.001%, optionally less than 0.0001%.

In some embodiments, the error rate includes an in/del error rate of less than 0.1%, optionally less than 0.01%.

In some embodiments, the disclosure relates generally to methods, as well as compositions, systems, kits and apparatuses, for nucleic acid sequencing, comprising: (a) providing a surface including one or more reaction sites that contain a nucleic acid template having, or hybridized to, an extendible end and a polymerase; (b) extending the extendible end by serially incorporating a plurality of nucleotides at the extendible end of at least one nucleic acid template using a polymerase, where at least one of the incorporated nucleotides is a reversible terminator nucleotide, and wherein the extending includes deblocking any incorporated reversible terminator nucleotide prior to next incorporation of a succeeding nucleotide; and (c) detecting at least two successive nucleotide incorporations and determining the identities of at least two successively incorporated nucleotides at a total error rate of less than 0.1%.

In some embodiments, the error rate includes an in/del error rate of less than 0.1%, optionally less than 0.01%.

In some embodiments, the total error rate is less than 0.01%.

In some embodiments, the total error rate includes a mismatch error rate of less than 0.001%, optionally less than 0.0001%.

In some embodiments, the total error rate includes an in/del error rate of less than 0.1%, optionally less than 0.01%.

In some embodiments, the disclosure relates generally to systems, as well as compositions, methods, kits and apparatuses, including a system for performing nucleotide incorporation, comprising: (a) a flow cell containing a surface including one or more reaction sites containing a polymerase and a nucleic acid template that has, or is hybridized to, an extendible end; (b) an inlet having one end connected to the flow cell and another end connected to a one or more reservoirs containing one or more types of terminator nucleotide; and (c) a sensor configured to detect a non-optical signal indicating a nucleotide incorporation occurring at least one of the reaction sites.

Additional objects, features, and/or advantages will be set forth in part in the description which follows, and in part will be obvious from the description, or may be learned by practice of the present disclosure and/or claims. At least some of these objects and advantages may be realized and attained by the elements and combinations particularly pointed out in the appended claims.

Throughout this application various publications, patents, and/or patent applications are referenced. The disclosures of these publications, patents, and/or patent applications in their entireties are hereby incorporated by reference into this application in order to more fully describe the state of the art to which this invention pertains.

It is to be understood that both the foregoing general description and the following detailed description are exemplary and explanatory only and are not restrictive of the claims; rather the claims should be entitled to their full breadth of scope, including equivalents.

DETAILED DESCRIPTION

This description and exemplary embodiments should not be taken as limiting. For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

In some embodiments, the disclosure relates generally to improved methods, systems, compositions and kits for nucleic acid analysis that involve the use of terminator nucleotides in a template-dependent nucleotide incorporation reaction (for example, a sequencing-by-synthesis reaction) in conjunction with non-optical detection of nucleotide incorporation. Such systems, methods, compositions and kits provide unique advantages over current systems, since current systems either use terminator-based sequencing chemistry in conjunction with optical labels and optical detection, or use non-optical detection with non-terminating nucleotides. The first category of systems, i.e., systems using optically labeled terminators, are subject to the technical limitations imposed by the need to discriminate between the different optical labels that are use to identify the underlying nucleotide type. For example, and as described above, in the systems providing by Illumina, Inc., and/or Intelligent Bio-Systems, Inc., and Pacific Biosystems, at least some of the 4 different types of nucleotides employed are typically labeled with a type-specific fluorescent label. Typically, there is at least some overlap or interference between the different labels, e.g., by quenching, colorimetric interference, or spectral interference. Such overlap or interference can lead to errors in nucleotide identification, thus ultimately limiting the accuracy of the sequencing system.

Similarly, systems using non-optical detection (e.g., Ion Torrent Systems, Inc.) typically do not use terminator nucleotides and instead perform template-dependent synthesis using non-terminator nucleotides, accompanied by detection of a non-optical signal indicating nucleotide incorporation. In such systems, different nucleotide types are successively flowed through a flowcell containing a template/primer complex bound to a polymerase. The resulting non-optical signal indicating the occurrence and degree of nucleotide incorporation is quantified to determine the number of nucleotides incorporated during the current nucleotide flow. However, as described elsewhere herein, such systems can be prone to inaccuracies in certain situations, such as analysis of nucleic acid templates containing homopolymer regions and/or insertions/deletions ("indels").

These above technical limitations (requirement for spectral resolution and discrimination of overlapping emission spectra on the one hand, and requirement for accurate quantification of non-optical signals indicating nucleotide incorporation based on a homopolymer region in the template) are collectively addressed through the new methods described herein involving sequencing by synthesis using semiconductor sensors to detect incorporation of unlabeled (or non-optically labeled) terminator nucleotides, Semiconductor sequencing is uniquely advantageous for terminator-like chemistries. The need for spectral resolution is avoided by the elimination of optical (e.g., fluorescent) labels. Similarly, the need for quantification of a nucleotide signal is avoided by ensuring that only one base is incorporated per nucleotide flow, prior to detection and identification of the incorporated nucleotide, even in the context of homopolymeric templates. As a result, the accuracy of the disclosed sequencing methods is exponentially higher than that of these current methods.

In some embodiments of the disclosure, solutions, termed nucleotide flows, containing a single base type each are repeatedly flowed over an array of sequencing reaction sites, and the signal from each site is measured. Unlike optical measurements which use labels that can be subject to spectral confusion, the signal generated during a particular nucleotide flow is measuring the unique addition of a single base type. This allows for a sharp distinction between incorporation and non-incorporation, similar to the existing high accuracy 1-mer vs 0-mer distinction found in semiconductor sequencing. Such methods therefore afford include vastly reduced sequencing error rates as compared either to current methods involving sequencing by synthesis using fluorescently labeled nucleotides (as exemplified in the sequencing systems provided by Illumina, Inc. and Intelligent Bio-Systems, Inc.) or using unlabeled and unblocked nucleotides (e.g., Ion Torrent™ PGM™ and Proton™ sequencing systems). For example, according to a recent peer-reviewed publication, the observed raw error rate is 0.8% for an Illumina MiSeq system, 0.76% for an Illumina GAIIx system, 0.26% for an Illumina HiSeq 2000, while the observed raw error rate for the Ion Torrent PGM system is 1.71%. See Quail et al., *A tale of three next generation sequencing platforms: comparison of Ion Torrent, Pacific Biosciences and Illumina Miseq sequencers,* BMC Genomics 13:341 (2012), incorporated by reference herein.

The relatively high error rate in the current Ion Torrent systems can be modeled as follows. For a template sequence CAAAG, with 10% of molecules out-of-phase by one base, using a repeated nucleotide flow order of TACG, the signals after each of the 4 nucleotide flows (T,A,C,G) would read (0,0,0.9,0), (0,0.9,0.1,0), (0,1.0,0,0),(0,1.0,0,0),(0,0.1,0,0.9), (0,0,0,0.1) in each set of 4 flows. Because the homopolymer signal is self-reinforcing, the signals in other base flows are reduced while reading through the homopolymer because the out-of-phase signals cannot be observed until the homopolymer (here, the triplet "AAA" in the template CAAAG) is completed.

The significant increase in sequencing accuracy afforded by the disclosed methods (and associated compositions, kits, systems and apparatuses) can be illustrated using computer simulations that predict the accuracy based on mathematical models. For example, assuming similar signal-to-noise as existing semiconductor sequencing chips (additive and multiplicative), the accuracy of the first 50 bases is estimated to achieve below 0.1% error, with homopolymers between 6 and 10 nucleotides in length achieving error rates of below 1%. See Figure Flow order, phase parameters, additive and multiplicative noise are similar to Ion PGM for this simulation. 10,000 random sequences of length 200 were generated and fed through a simulated sequencing process, involving over 2 million simulated bases of sequencing. The results are that the theoretical mismatch rate (all else remaining equal to the PGM) is 0.00034 percent, far below any existing platform. The theoretical in/del rate is 0.014%, also far exceeding any existing platform for accuracy. To obtain these results, each generated sequence is aligned using a standard smith-waterman local alignment to the reconstructed sequence after the simulated experiment. This is done using the "pairwiseAlignment" function from the R Biostrings package with typical gap penalties.

The count of base positions where mismatches occur is summed over all sequences and divided by the total number of bases in the generated sequences to find the mismatch rate per original base. This is then multiplied by 100 to turn it into a percentage. The standard "nmismatch" function for analyzing alignments is used here to recover the number of mismatches. Similarly, the sum of all gap lengths within insertions and deletions is found, and divided by the total number of bases in the generated sequences to obtain an insertion and deletion rate per original base. This is also multiplied by 100 to turn it into a percentage. The standard "nindel" function for analyzing alignments is used here to recover the total gap size of insertions and deletions.

The disclosed methods (and related systems, compositions, kits and apparatuses) also possess the additional advantage that, unlike optical systems that incorporate multiple bases simultaneously, phase-correcting flow orders may be used to rejoin out-of-phase populations of molecules by appropriately structured sequences of solutions being applied. Use of phase-correcting flow orders has been described previously in U.S. Publ. No. 20120264621 (U.S. Ser. No. 13/440,849), incorporated by reference herein. In this way incomplete extension of molecules may be ameliorated efficiently, as demonstrated by the use of such flow orders with other non-optical detection sequencing systems, such as the Ion Torrent™ PGM™ sequencer.

In some embodiments, the disclosure relates generally to methods and associated compositions, systems and kits, for obtaining nucleic acid sequence information from a nucleic acid template molecule. Optionally, the disclosed methods, compositions and systems involve a reaction site or array of reaction sites, where independent nucleotide incorporation reactions at the reaction sites in the array. Optionally, the reaction site (or one or more reaction sites within an array of reaction sites) is attached or operatively linked to a non-optical sensor. In some embodiments, different reaction sites in the array are attached or operatively linked to different sensors. In some embodiments, at least two of the reaction sites are attached or operatively linked to the same sensor.

The sensor can be configured to detect a non-optical signal that indicates a template-dependent nucleotide incorporation occurring at the reaction site or sites to which it is attached or operatively linked. In some embodiments, the non-optical signal does not include photon emissions. In some embodiments, the nucleotide incorporation can include incorporation of a terminator nucleotide. In some embodiments, the nucleotide incorporation can include incorporation of a non-terminator nucleotide. The terminator nucleotide may include a reversible or a non-reversible terminator moiety. The reversible terminator moiety may be removable. For example, the reversible terminator moiety may be removed through physical or chemical treatments.

Optionally, the terminator nucleotide does not include an optically detectable label. In some embodiments, the terminator nucleotide does not include a fluorescent or luminescent label. In some embodiments, the terminator nucleotide does not include a label that can be detected spectrally.

In some embodiments, the disclosed methods, compositions and systems involve performing template-dependent nucleotide incorporation at a single reaction site, or at a plurality of reaction sites in an array of reaction sites. Different types of nucleotides may be flowed sequentially across the reaction site (each flow of nucleotide termed a "nucleotide flow" herein), and incorporation will occur when the incoming nucleotide is complementary to the nucleotide in the template strand immediately adjacent to the extendible end of the synthesized nucleic acid molecule. In some embodiments, a terminator nucleotide is flowed across the reaction site and its incorporation (or lack thereof) is detected using the semiconductor sensor. Optionally, the next nucleotide flowed across the reaction site is a terminator nucleotide. Optionally, the next nucleotide flowed across the reaction site is not a terminator nucleotide. Nucleotides that are not terminators are referred to herein as non-terminator nucleotides. In some embodiments, a series of nucleotide flows across the reaction site are performed. Optionally, all or some of the nucleotide flows include terminator nucleotides. In some embodiments, a series of nucleotide flows are performed that include terminator nucleotides, followed by a series of flows of nucleotide flows that include non-terminator nucleotides that do not have terminating properties. In some embodiments, a flow containing a single type of terminator nucleotide is succeeded by a flow containing a single type of non-terminator nucleotide. In some embodiments, a series of flows contain terminator nucleotides are performed, followed by a series of flows containing non-terminator nucleotides. In some embodiments, a series of flows containing non-terminator nucleotides is followed by a series of flows containing terminator nucleotides. Optionally, a first series of nucleotide flows is succeeded by a denaturing step. For example, the denaturing step can involve application of heat and/or chemicals that denature the synthesized strand from the template strand. In some embodiments, the denaturing step includes performing a denaturing flow. The denaturing flow can include flow of a denaturing agent (e.g. urea, formamide, alkali, NaOH and the like) across one or more reaction sites. The reaction sites can each act as a site for sequencing by synthesis. The denaturing agent can denature the synthesized strand from the template strand. Optionally, a first series of nucleotide flows is succeeded by a denaturing flow, following by a second series of nucleotide flows. In some embodiments, at least one nucleotide flow in the first series includes terminator nucleotides. In some embodiments, at least one nucleotide flow in the first series includes non-terminator nucleotides. In some embodiments, at least one nucleotide flow in the second series includes terminator nucleotides. In some embodiments, at least one nucleotide flow in the second series includes non-terminator nucleotides. In some embodiments, all of the nucleotide flows in the first series include terminator nucleotides. In some embodiments, all of the nucleotide flows in the second series include non-terminator nucleotides. In some embodiments, all of the nucleotide flows in the first series include non-terminator nucleotides. In some embodiments, all of the nucleotide flows in the second series include terminator nucleotides.

In some embodiments, the disclosed methods, compositions and systems can involve detection of the non-optical signal using a sensor attached to, or operatively linked to, the reaction site or sites. In some embodiments, the non-optical signal is a chemical signal indicating the release of nucleotide incorporation byproducts or generation of other chemical moieties. In some embodiments, the non-optical signal quantitatively indicates nucleotide incorporation. Optionally, the non-optical signal is a pH based signal. The pH based signal can be generated via the release of hydrogen ion byproducts during nucleotide incorporation. In some embodiments, the non-optical signal includes generation of phosphate or other ions at the reaction site or sites. In some embodiments, the non-optical signal includes generation of heat at the reaction site or sites.

As used herein, the term "nucleotide" and its variants refer to any compound that can bind selectively to, or can be polymerized by, a polymerase. Typically, but not necessarily, selective binding of the nucleotide to the polymerase is followed by polymerization of the nucleotide into a nucleic acid strand by the polymerase. Such nucleotides include not only naturally-occurring nucleotides but also any analogs or derivatives that, regardless of their structure, can bind selectively to and can optionally be polymerized by, a polymerase. While naturally-occurring nucleotides typically comprise sugar, base, and phosphate moieties, the nucleotides can include compounds lacking any one, some or all of such moieties, or can include one or more substitute groups.

In some embodiments, the nucleotide comprises a suitable sugar moiety, such as carbocyclic moiety (Ferraro and Gotor 2000 Chem. Rev. 100: 4319-48), acyclic moieties (Martinez, et al., 1999 Nucleic Acids Research 27: 1271-1274; Martinez, et al., 1997 Bioorganic & Medicinal Chemistry Letters vol. 7: 3013-3016), and other suitable sugar moieties (Joeng, et al., 1993 J. Med. Chem. 36: 2627-2638; Kim, et al., 1993 J. Med. Chem. 36: 30-7; Eschenmosser 1999 Science 284: 2118-2124.; and U.S. Pat. No. 5,558,991).

In some embodiments, the nucleotides comprise a base moiety. The base moiety can include substituted or unsubstituted nitrogen-containing parent heteroaromatic ring which is commonly found in nucleic acids, including naturally-occurring, substituted, modified, engineered variants, or analog nucleotides. In some embodiments, the base is a non-naturally occurring base. Typically, the base is capable of undergoing base pairing with another base according to a predetermined paradigm. For example, in some embodiments, the base is capable of forming Watson-Crick and/or Hoogstein hydrogen bonds with an appropriate complementary base. Alternatively, the base can be capable of base pairing according to a set of preestablished rules that do not include Watson-Crick pairings. Exemplary bases include, but are not limited to, purines and pyrimidines such as: 2-aminopurine, 2,6-diaminopurine, adenine (A), ethenoadenine, $N^6$-$\Delta^2$-isopentenyladenine (6iA), $N^6$-$\Delta^2$-isopentenyl-2-methylthioadenine (2ms6iA), $N^6$-methyladenine, guanine (G), isoguanine, $N^2$-dimethylguanine (dmG), 7-methylguanine (7mG), 2-thiopyrimidine, 6-thioguanine (6sG), hypoxanthine and $O^6$-methylguanine; 7-deaza-purines such as 7-deazaadenine (7-deaza-A) and 7-deazaguanine (7-deaza-G); pyrimidines such as cytosine (C), 5-propynylcytosine, isocytosine, thymine (T), 4-thiothymine (4sT), 5,6-dihydrothymine, $O^4$-methylthymine, uracil (U), 4-thiouracil (4sU) and 5,6-dihydrouracil (dihydrouracil; D); indoles such as nitroindole and 4-methylindole; pyrroles such as nitropyrrole; nebularine; inosines; hydroxymethylcytosines; 5-methycytosines; base (Y); as well as methylated, glycosylated, and acylated base moieties; and the like. Additional exemplary bases can be found in Fasman, 1989, in "Practical Handbook of Biochemistry and Molecular Biology", pp. 385-394, CRC Press, Boca Raton, Fla.

In some embodiments, the nucleotides can optionally include a chain of phosphorus atoms. The chain can include three, four, five, six, seven, eight, nine, ten or more phosphorus atoms. In some embodiments, the phosphorus chain can be attached to any carbon of a sugar ring, such as the 2', 3' or 5° carbon. The phosphorus chain can be linked to the sugar with an intervening O or S. In one embodiment, one or more phosphorus atoms in the chain can be part of a phosphate group having P and O. In another embodiment, the phosphorus atoms in the chain can be linked together with intervening O, NH, S, methylene, substituted methylene, ethylene, substituted ethylene, $CNH_2$, $C(O)$, $C(CH_2)$, $CH_2CH_2$, or $C(OH)CH_2R$ (where R can be a 4-pyridine or 1-imidazole). In one embodiment, the phosphorus atoms in the chain can have side groups having O, $BH_3$, or S. At least one phosphorus atom can be part of a phosphate group. In the phosphorus chain, a phosphorus atom with a side group other than O can be a substituted phosphate group. Some examples of nucleotide analogs having more than three phosphorus groups are described in Xu, U.S. Pat. No. 7,405,281. The phosphate groups include analogs, such as phosphoramidate, phosphorothioate, phosphorodithioate, and O-methylphosphoroamidite groups. At least one of the phosphate groups can be substituted with a fluoro and/or chloro group. The phosphate groups can be linked to the sugar moiety by an ester or phosphoramide linkage.

In some embodiments, the nucleotides include ribonucleotides, deoxyribonucleotides, ribonucleotide polyphosphate molecules, deoxyribonucleotide polyphosphate molecules, peptide nucleotides, nucleoside polyphosphate molecules, metallonucleosides, phosphonate nucleosides, and modified phosphate-sugar backbone nucleotides, and any analogs or variants of the foregoing.

In some embodiments, the nucleotide is a terminator nucleotide. Typically, the terminator nucleotide can be incorporated into an extendible end of a nucleic acid molecule. In some embodiments, the terminator nucleotide will, once incorporated, inhibit or block further nucleotide incorporations at the end of the nucleic acid molecule. The incorporation of the terminator nucleotide can convert the extendible end into a non-extendible end. Optionally, the terminator nucleotide includes a terminator group (also referred to as a terminator moiety) that confers the ability to inhibit or block further nucleotide incorporations. In some embodiments, the terminator nucleotides can be operably linked to at least one terminator group or moiety. In some embodiments, the terminator group can be neutralized, cleaved, or otherwise removed from the terminator nucleotide via suitable treatments. In some embodiments, neutralization, cleavage or removal of the terminator group can permit subsequent nucleotide incorporations to occur. In some embodiments, the non-extendible end can be converted to an extendible end via cleavage, neutralization or removal of the terminator group.

Alternatively, the nucleotide can be a non-terminator nucleotide. The non-terminator nucleotide can include any nucleotide (including structural or functional equivalents thereof) that, once incorporated into an extendible end, do not inhibit or block the subsequent incorporation of another nucleotide into the extendible end. In some embodiments, the non-terminator nucleotide is a nucleotide that does not include a terminator moiety.

In some embodiments, a terminator nucleotide comprises a terminator moiety or group which permits incorporation of the terminator nucleotide but inhibits incorporation of a subsequent nucleotide. In some embodiments, the terminator moiety can be removable or cleaved with an enzyme, heat, chemical or light. In some embodiments, the terminator moiety is not removable. In another embodiment, the terminator nucleotide can be labeled or un-labeled. In some embodiments, the terminator nucleotide does not include an optically detectable label. In some embodiments, the terminator nucleotide does not include a fluorescent or luminescent group. In some embodiments, the terminator nucleotide includes a label that is not optically detectable (referred to herein as a non-optical label). The non-optical label can include a molecule, a chemical moiety, a compound, a radioisotope, a Raman label, an NMR label, a polynucleotide, an oligonucleotide, a protein, an antibody, a member of a binding pair (e.g., a biotin/avidin binding pair), an enzyme, an enzyme substrate, and the like.

As used herein, the term "nucleotide" and its variants refer to any compound that can bind selectively to, or can be polymerized by, a polymerase. Typically, but not necessarily, selective binding of the nucleotide to the polymerase is followed by polymerization of the nucleotide into a nucleic acid strand by the polymerase. Such nucleotides include not only naturally-occurring nucleotides but also any analogs or derivatives that, regardless of their structure, can bind selectively to and can optionally be polymerized by, a polymerase. While naturally-occurring nucleotides typically comprise sugar, base, and phosphate moieties, the nucleotides can include compounds lacking any one, some or all of such moieties, or can include one or more substitute groups. In some embodiments, nucleotides used according to the disclosure can be operably linked to one or more reporter moiety (e.g., labeled nucleotides) or can be unlabeled. In some embodiments, the nucleotides comprise incorporatable, or non-incorporatable nucleotides. The nucleotides can include reversible terminator nucleotides and non-reversible terminator nucleotides.

In some embodiments, the disclosed nucleotide incorporation methods result in the formation and continued extension of a synthesized strand of nucleic acid, referred to herein as the synthesized nucleic acid molecule or the synthesized strand. The synthesized strand typically includes an extendible end (also referred to herein as a "polymerization initiation site"). The extendible end can serve as the site of nucleotide incorporation; incorporation of a nucleotide into the extendible end will result in the extension of the synthesized strand and increase in length of the synthesized strand by one nucleotide. Typically, the nucleotide incorporation is performed in a template-dependent manner where the identity of the incorporated nucleotide is determined based on the identity of an opposing nucleotide in the nucleic acid template, as dictated by a predetermined base pairing paradigm. The nucleotide incorporation can be performed using a polymerase (e.g., DNA or RNA polymerase) to polymerize one or more nucleotides. In some embodiments, the extendible end can include a terminal 3' OH group. The 3' OH group can serve as a substrate for the polymerase for nucleotide polymerization. The 3' OH group can serve as a substrate for the polymerase to form a phosphodiester bond between the terminal 3' OH group and an incorporated nucleotide. The 3' OH group can be provided by: the terminal end of a primer molecule; a nick or gap within a nucleic acid molecule (e.g., oligonucleotide) which is base-paired with the target molecule; the terminal end of a secondary structure (e.g., the end of a hairpin-like structure); or an origin of replication. Thus, the extendible end may be at a terminal end or within a base-paired nucleic acid molecule. In other embodiments, the extendible end used by some polymerases (e.g., RNA polymerase) may not include a 3'OH group.

In some embodiments, the disclosure relates generally to methods, as well as compositions, systems, kits and apparatuses, comprising incorporating a nucleotide.

In some embodiments, methods for incorporating a nucleotide comprise providing a surface.

In some embodiments, the surface includes one or more reaction sites.

Optionally, the surface includes a plurality of reaction sites organized in an ordered or random arrangement.

Optionally, the surface includes an array of a plurality of reaction sites.

Optionally, the reaction sites include wells, chambers, cavities, or a location on the surface.

Optionally, at least one reaction site contains a sensor.

Optionally, at least on reaction site is attached or is operably linked to a sensor.

In some embodiments, the sensor detects changes in ions (e.g., hydrogen ions), protons, phosphate groups, including pyrophosphate groups.

In some embodiments, the sensor can detect at least one by product or cleavage product of a nucleotide incorporation reaction, including pyrophosphate, hydrogen ions, charge transfer, or heat.

In some embodiments, at least one reaction site contains one or more polymerases.

Optionally, at least one reaction site is attached to one or more polymerases.

Optionally, a polymerase can be attached to a reaction site by a linker.

Optionally, one or more polymerases is located within a reaction site, and the polymerase is not attached to the reaction site.

In some embodiments, the polymerase comprises a DNA-dependent DNA polymerase or an RNA-dependent DNA polymerase.

Optionally, the polymerase is heat-stable or heat-labile.

In some embodiments, at least one reaction site further includes one or more nucleic acid templates (e.g., template polynucleotides).

Optionally, the nucleic acid templates comprise single- or double-stranded nucleic acids.

In some embodiments, the nucleic acid template is hybridized to an extendible end.

Optionally, the nucleic acid is hybridize to an oligonucleotide primer having an extendible end.

In some embodiments, the nucleic acid template has an extendible end.

Optionally, the nucleic acid template forms a self-priming extendible end.

In some embodiments, the extendible end includes a terminal 3' OH group.

In some embodiments, methods for incorporating a nucleotide comprises providing a surface which includes one or more reaction sites, the reaction sites containing at least one polymerase and one or more nucleic acid templates.

In some embodiments, methods for incorporating a nucleotide further comprise performing a first nucleotide flow.

Optionally, the first nucleotide flow can be performed by contacting one or more of the reaction sites with a first solution.

Optionally, the first solution contains one or more terminator nucleotides and/or non-terminator nucleotides.

Optionally, the first solution includes a single type or a plurality of different types of terminator nucleotides.

In some embodiments, the first solution includes any one or any combination of adenosine, guanosine, cytosine, thymidine and/or uridine terminator nucleotides.

Optionally the first solution includes at least one compound that enhances polymerase activity for incorporating a nucleotide, including for example any one or any combination of magnesium, manganese and/or ATP.

Optionally, the first solution is flowed onto one or more reaction sites, to bring the nucleotides contained in the first solution in contact with the polymerases and/or the nucleic acid templates at the reaction sites.

In some embodiments, methods for incorporating a nucleotide further comprise incorporating at least one terminator nucleotide into the nucleic acid template.

Optionally, at least one reaction site includes one or more polymerases that incorporates at least one terminator nucleotide into the nucleic acid template.

Optionally, the polymerase at the reaction site incorporates at least one terminator nucleotide at the extendible end of the nucleic acid template.

In some embodiments, at least one reaction site contains a complex having a polymerase bound to a nucleic acid template which has an extendible end, where the extendible end includes a terminal nucleotide having a 3'OH group. In some embodiments, the polymerase (as part of the complex) binds to an incoming terminator nucleotide, where the incoming terminator nucleotide is complementary to a target nucleotide located on the nucleic acid template. In some embodiments, methods for conducting a nucleotide incorporation reaction which is mediated by the polymerase, comprises: (a) contacting (i) the polymerase which is part of a complex having a polymerase bound to a nucleic acid template having an extendible end and (ii) an incoming terminator nucleotide, wherein the complex is at a reaction site; and (b) catalyzing bond formation between the incoming terminator nucleotide and a nucleotide at the extendible end, by polymerase-mediated phosphodiester bond formation between the incoming terminator nucleotide and the nucleotide at the extendible end, with concomitant cleavage between the α and β phosphate groups of the incoming terminator nucleotide to form a cleavage product. In some embodiments, the cleavage products include any one or a combination of phosphate-based compounds, protons, and/or hydrogen ions. Optionally, the phosphate-based compounds include pyrophosphate. In some embodiments, the polymerase liberates the cleavage product. Optionally, the liberated cleavage product dissipates within the nucleotide incorporation reaction mixture and contacts at least one sensor located at a reaction site. In some embodiments, the sensor detects the presence of one or more cleavage products produced during incorporation of the terminator nucleotide. For example the sensor detects phosphate-based compounds, protons, and/or hydrogen ions. In some embodiments, the cleavage products are non-optically detected by the sensors at the reaction sites. In some embodiments, the sensor detects the presence of one or more cleavage products which are produced by incorporation of the terminator nucleotide, and the sensor produces a signal. Thus, the signal produced by the sensor correlates with incorporation of the terminator nucleotide. Optionally, the method further comprises analyzing the signal produced by the sensor. Optionally, the method further comprises identifying the incorporated nucleotide. In some embodiments, the incoming terminator nucleotide contacts the polymerase by performing a first nucleotide flow. In some embodiments, the terminator nucleotide that is incorporated contains a blocking group. In some embodiments, the blocking group is removable or can be transformed to become an extendible end. In some embodiments, the terminator nucleotide that is incorporated includes adenosine, guanosine, cytosine, thymidine or uridine. In some embodiments, methods for conducting a nucleotide incorporation reaction further comprise incorporating a subsequent nucleotide, which optionally includes de-blocking the blocking group on the incorporated terminator nucleotide. In some embodiments, the blocking group (of the incorporated nucleotide) is removable by enzyme, chemical, light or heat, or can be transformed to become an extendible end (e.g., terminal 3'OH group). In some embodiments, the polymerase-template complex at the reaction site can be contacted with a second nucleotide flow which contains terminator nucleotides and/or non-terminator nucleotides, and a second nucleotide is incorporated.

Optionally, the second nucleotide flow can be performed by contacting one or more of the reaction sites with a second solution.

Optionally, the second solution contains one or more nucleotides, where the nucleotides contact the polymerases and/or the nucleic acid templates at the reaction sites.

Optionally, the second solution includes a single type or a plurality of different types of terminator nucleotides.

Optionally, the second solution includes one or more types of terminator nucleotides.

In some embodiments, the second solution includes any one or any combination of adenosine, guanosine, cytosine, thymidine and/or uridine terminator nucleotides.

Optionally the second solution includes at least one compound that enhances polymerase activity for incorporating a nucleotide.

Optionally, the second solution includes any one or any combination of magnesium, manganese and/or ATP.

Optionally, the second solution includes at least one non-terminator nucleotide.

In some embodiments, the second solution includes a single type or a plurality of different types of non-terminator nucleotides.

Optionally, the second solution is flowed onto one or more reaction sites, to bring the nucleotides contained in the second solution in contact with the polymerases and/or the nucleic acid templates at the reaction sites.

In some embodiments, methods for nucleotide incorporation further comprise performing a first series of nucleotide flows.

In some embodiments, methods for nucleotide incorporation further comprise performing a first series of nucleotide flows, by contacting the polymerases and/or nucleic acids at the reaction sites with at least a first and a second nucleotide flow.

Optionally, the first series of nucleotide flows comprises two or more nucleotide flows.

Optionally, each nucleotide flow in the first series of nucleotide flows includes contacting one or more reaction sites with a solution of nucleotides.

Optionally, the solution of nucleotides, in the first series of nucleotide flows, contains one or more nucleotide types.

In some embodiments, methods for nucleotide incorporation further comprise detecting nucleotide incorporation.

In some embodiments, the detecting includes detecting changes in ions (e.g., hydrogen ions), protons, phosphate groups, including pyrophosphate groups.

In some embodiments, the detecting include non-optical detecting at least one cleavage product from a nucleotide incorporation reaction.

In some embodiments, the detecting includes detecting the presence of at least one cleavage product from a nucleotide incorporation reaction, where the cleavage products include a phosphate-based compounds, protons, and/or hydrogen ions. Optionally, the phosphate-based compounds include pyrophosphate.

In some embodiments, detecting nucleotide incorporation includes detecting a non-optical signal that indicates that nucleotide incorporation has occurred.

Optionally, the nucleotide incorporation is detected using a sensor.

Optionally, the sensor is attached or operatively linked to at least one reaction sites.

Optionally, the sensor detects the non-optical signal that is associated with a nucleotide incorporation event.

In some embodiments, methods for nucleotide incorporation further comprise detecting nucleotide incorporation, wherein the nucleotide incorporation occurs at the one or more reaction sites.

In some embodiments, methods for nucleotide incorporation further comprise detecting a lack of nucleotide incorporation (e.g., low or no signal).

In some embodiments, methods for nucleotide incorporation further comprise detecting a lack of nucleotide incorporation at the one or more reaction sites.

Optionally, the detecting step is performed after each nucleotide flow in a first series of nucleotide flows.

Optionally, the detecting step is performed prior to a subsequent nucleotide flow in the first series of nucleotide flows.

Optionally, the detecting step is performed after a first nucleotide flow in the first series of nucleotide flows.

Optionally, the detecting step is performed after a second nucleotide flow in the first series of nucleotide flows.

Optionally, the detecting step is performed prior to the second nucleotide flow in the first series of nucleotide flows.

In some embodiments, methods for nucleotide incorporation further comprise performing a second series of nucleotide flows.

Optionally, the second series of nucleotide flows comprises two or more nucleotide flows.

Optionally, each nucleotide flow in the second series of nucleotide flows includes contacting one or more reaction sites with a solution of nucleotides.

Optionally, the solution of nucleotides, in the second series of nucleotide flows, contains one or more nucleotide types.

In some embodiments, methods for nucleotide incorporation include terminator nucleotides which comprise reversible terminator nucleotides.

In some embodiments, a reversible terminator nucleotide comprises a nucleotide linked to a blocking moiety, where the blocking moiety is linked to any portion of the base, sugar or any phosphate group, and the blocking moiety is removable.

In some embodiments, the terminator nucleotides include 3' OH unblocked nucleotides. For example, the terminator nucleotides comprise a blocking group linked to any portion of the base. In some embodiments, the blocking group that is linked to the base inhibits polymerase-mediated incorporation of a subsequent nucleotide. Optionally, the blocking group can be linked to the N7 or O6 positions of a purine, or C5 position of a pyrmidine. Optionally, the blocking group includes a 2-nitrobenzyl or nitrobenzyloxy group, or derivative thereof. Optionally, the terminator nucleotides include a detectable label (e.g., fluorophore) linked to the blocking group. In some embodiments, the blocking group and/or label are attached to a linker which is optionally cleavable with a chemical, light, or enzyme. Optionally, the linker is cleavable with palladium compounds (e.g., sodium tetrachoropalladate (II), or palladium on activated carbon). See for example U.S. Pat. Nos. 8,497,360; 8,148,503; 7,897,737; and 8,361,727, which are expressly incorporated herein by reference as if set forth in full.

In some embodiments, the terminator nucleotides include 3' OH unblocked nucleotides. For example, the terminator nucleotides comprise a blocking group linked to any portion of the base. In some embodiments, the blocking group that is linked to the base inhibits polymerase-mediated incorporation of a subsequent nucleotide. Optionally, the blocking group can be linked to the NH group or C4 of a cytosine base, or linked to the P group or C4 of a uracil or thymine base, or linked to the N7 of a purine base. Optionally, the blocking group is a benzyl group. Optionally, the alpha carbon of the benzyl group is substituted with one alkyl or aryl group. In some embodiments, the benzyl group can be functionalized to increase the blocking effects. In some embodiments, the benzyl group is non-cleavable. In some embodiments, the blocking group can be linked to a fluorophore (dye) via a cleavable linker, which is optionally cleavable with a chemical, light, or enzyme. Optionally, the linker is cleavable with palladium compounds (e.g., sodium tetrachoropalladate (II), or palladium on activated carbon). See for example U.S. Pat. Nos. 7,893,227; 8,198,029; and 7,964,352, which are expressly incorporated herein by reference as if set forth in full.

In some embodiments, the terminator nucleotides include nucleotides that are linked at the base with a detectable label. Optionally, the linker includes an allylic system. In some embodiments, the detectable labels includes a dye (e.g., optically-detectable dye), or a biotin-streptavidin system. In some embodiments, the detectable label acts as blocking group. Optionally, the detectable label can be linked to the 7-position of a purine or deazapurine, or the N-6 position of a modified adenosine or N-2 position of a modified guanine. Optionally, the detectable label can be linked to the 5 position of a pyrimidine, such as cytidine, thymidine or uracil, or the N-4 position of a cytosine. In some embodiments, the linkers include: a disulfide linkage, acid labile linkers (e.g., dialkoxybenzyl linkers), Sieber linkers, indole linkers, and t-butyl Sieber linkers. Optionally, the linkers are cleavable linkers, and include: electrophilically-cleavable linkers, nucleophilically-cleavable linkers, photocleavable linkers, and linkers cleavable under reductive or oxidative conditions. Optionally, the linkers are cleavable via use of safety-catch linkers, and linkers cleavable by elimination mechanisms. See for example U.S. Pat. No. 7,785,796, which is expressly incorporated herein by reference as if set forth in full.

In some embodiments, the terminator nucleotides include nucleotides that are linked at the base with a detectable label. For example, a 7-deazapurine base can be linked at the 7-position. Optionally, the linker attaching the base to the detectable label can be an acid labile linker, a photocleavable linker, disulfide linkage, dialkoxybenzyl linkers, Sieber linkers, indole linkers, or t-butyl Sieber linkers. Optionally, the linker that attaches the base to the detectable label can be cleavable under oxidation conditions, or cleavable with a palladium compound, or cleavable with thiophilic metals, including nickel, silver or mercury. In some embodiments, the terminator nucleotides also include a blocking group linked to the 2' or 3' sugar position by a linker. For example, the blocking group includes an azido group. In some embodiments, the linker attached to the base and the linker attached to the 2' or 3' sugar position are cleavable under the same conditions. See for example, U.S. Pat. Nos. 7,057,026; 7,566,537 and 8,158,346, which are expressly incorporated herein by reference as if set forth in full.

In some embodiments, the terminator nucleotides include nucleotides that are linked at the base with a detectable label. For example the linker comprises a photocleavable linker. Optionally, the cleavable linker comprises a nitrobenzyl moiety. In some embodiments, the terminator nucleotide can be linked at the 3' sugar position with a blocking group. Optionally, the blocking group comprises a small moiety. Exemplary small moieties include —$CH_2OCH_3$ (MOM) or —$CH_2CH{=}CH_2$ (allyl;). See for example, U.S. Pat. Nos. 7,713,698; 7,790,869; 8,088,575; 7,635,578; and 7,883,869, which are expressly incorporated herein by reference as if set forth in full.

In some embodiments, methods for nucleotide incorporation include a sensor comprises an ISFET.

In some embodiments, any nucleic acid template can be sequenced by any sequencing method, including sequencing-by-synthesis, ion-based sequencing involving the detection of sequencing byproducts using field effect transistors (e.g., FETs and ISFETs), chemical degradation sequencing, ligation-based sequencing, hybridization sequencing, pyrophosphate detection sequencing, capillary electrophoresis, gel electrophoresis, next-generation, massively parallel sequencing platforms, sequencing platforms that detect hydrogen ions or other sequencing by-products, and single molecule sequencing platforms. In some embodiments, a sequencing reaction can be conducted using at least one sequencing primer that can hybridize to any portion of the nucleic acid templates, including a nucleic acid adaptor or a target polynucleotide.

In some embodiments, any nucleic acid template can be sequenced using methods that detect one or more byproducts of nucleotide incorporation. The detection of polymerase extension by detecting physicochemical byproducts of the extension reaction, can include pyrophosphate, hydrogen ion, charge transfer, heat, and the like, as disclosed, for example, in U.S. Pat. No. 7,948,015 to Rothberg et al.; and Rothberg et al, U.S. Patent Publication No. 2009/0026082, hereby incorporated by reference in their entireties. Other examples of methods of detecting polymerase-based extension can be found, for example, in Pourmand et al, Proc. Natl. Acad. Sci., 103: 6466-6470 (2006); Purushothaman et al., IEEE ISCAS, IV-169-172; Anderson et al, Sensors and Actuators B Chem., 129: 79-86 (2008); Sakata et al., Angew. Chem. 118:2283-2286 (2006); Esfandyapour et al., U.S. Patent Publication No. 2008/01666727; and Sakurai et al., Anal. Chem. 64: 1996-1997 (1992).

Reactions involving the generation and detection of ions are widely performed. The use of direct ion detection methods to monitor the progress of such reactions can simplify many current biological assays. For example, template-dependent nucleic acid synthesis by a polymerase can be monitored by detecting hydrogen ions that are generated as natural byproducts of nucleotide incorporations catalyzed by the polymerase. Ion-sensitive sequencing (also referred to as "pH-based" or "ion-based" nucleic acid sequencing) exploits the direct detection of ionic byproducts, such as hydrogen ions, that are produced as a byproduct of nucleotide incorporation. In one exemplary system for ion-based sequencing, the nucleic acid to be sequenced can be captured in a microwell, and nucleotides can be flowed across the well, one at a time, under nucleotide incorporation conditions. The polymerase incorporates the appropriate nucleotide into the growing strand, and the hydrogen ion that is released can change the pH in the solution, which can be detected by an ion sensor that is coupled with the well. This technique does not require labeling of the nucleotides or expensive optical components, and allows for far more rapid completion of sequencing runs. Examples of such ion-based nucleic acid sequencing methods and platforms include the Ion Torrent PGM™ or Proton™ sequencer (Ion Torrent™ Systems, Life Technologies Corporation).

In some embodiments, amplified target nucleic acids produced using the methods, systems and kits of the present teachings can be used as a substrate for a biological or chemical reaction that is detected and/or monitored by a sensor including a field-effect transistor (FET). In various embodiments the FET is a chemFET or an ISFET. A "chemFET" or chemical field-effect transistor, is a type of field effect transistor that acts as a chemical sensor. It is the structural analog of a MOSFET transistor, where the charge on the gate electrode is applied by a chemical process. An "ISFET" or ion-sensitive field-effect transistor, is used for measuring ion concentrations in solution; when the ion concentration (such as H+) changes, the current through the transistor will change accordingly. A detailed theory of operation of an ISFET is given in "Thirty years of ISFETOLOGY: what happened in the past 30 years and what may happen in the next 30 years," P. Bergveld, Sens. Actuators, 88 (2003), pp. 1-20.

In some embodiments, the FET may be a FET array. As used herein, an "array" is a planar arrangement of elements such as sensors or wells. The array may be one or two dimensional. A one dimensional array can be an array having one column (or row) of elements in the first dimension and a plurality of columns (or rows) in the second dimension. The number of columns (or rows) in the first and second dimensions may or may not be the same. The FET or array can comprise $10^2$, $10^3$, $10^4$, $10^5$, $10^6$, $10^7$ or more FETs.

In some embodiments, one or more microfluidic structures can be fabricated above the FET sensor array to provide for containment and/or confinement of a biological or chemical reaction. For example, in one implementation, the microfluidic structure(s) can be configured as one or more wells (or microwells, or reaction chambers, or reaction wells, as the terms are used interchangeably herein) disposed above one or more sensors of the array, such that the one or more sensors over which a given well is disposed detect and measure analyte presence, level, and/or concentration in the given well. In some embodiments, there can be a 1:1 correspondence of FET sensors and reaction wells.

Microwells or reaction chambers are typically hollows or wells having well-defined shapes and volumes which can be manufactured into a substrate and can be fabricated using conventional microfabrication techniques, e.g. as disclosed in the following references: Doering and Nishi, Editors, Handbook of Semiconductor Manufacturing Technology, Second Edition (CRC Press, 2007); Saliterman, Fundamentals of BioMEMS and Medical Microdevices (SPIE Publications, 2006); Elwenspoek et al, Silicon Micromachining (Cambridge University Press, 2004); and the like. Examples of configurations (e.g. spacing, shape and volumes) of microwells or reaction chambers are disclosed in Rothberg et al, U.S. patent publication 2009/0127589; Rothberg et al, U.K. patent application GB24611127.

In some embodiments, the biological or chemical reaction can be performed in a solution or a reaction chamber that is in contact with, operatively coupled, or capacitively coupled to a FET such as a chemFET or an ISFET. The FET (or chemFET or ISFET) and/or reaction chamber can be an array of FETs or reaction chambers, respectively.

In some embodiments, a biological or chemical reaction can be carried out in a two-dimensional array of reaction chambers, wherein each reaction chamber can be coupled to a FET, and each reaction chamber is no greater than 10 μm$^3$ (i.e., 1 pL) in volume. In some embodiments each reaction chamber is no greater than 0.34 pL, 0.096 pL or even 0.012 pL in volume. A reaction chamber can optionally be no greater than 2, 5, 10, 15, 22, 32, 42, 52, 62, 72, 82, 92, or 102 square microns in cross-sectional area at the top. Preferably, the array has at least $10^2$, $10^3$, $10^4$, $10^5$, $10^6$, $10^7$, $10^8$, $10^9$, or more reaction chambers. In some embodiments, at least one of the reaction chambers is operatively coupled to at least one of the FETs.

FET arrays as used in various embodiments according to the disclosure can be fabricated according to conventional CMOS fabrications techniques, as well as modified CMOS fabrication techniques and other semiconductor fabrication techniques beyond those conventionally employed in CMOS fabrication. Additionally, various lithography techniques can be employed as part of an array fabrication process.

Exemplary FET arrays suitable for use in the disclosed methods, as well as microwells and attendant fluidics, and methods for manufacturing them, are disclosed, for example, in U.S. Patent Publication No. 2010/0301398; U.S. Patent Publication No. 2010/0300895; U.S. Patent Publication No. 2010/0300559; U.S. Patent Publication No. 2010/0197507, U.S. Patent Publication No. 2010/0137143; U.S. Patent Publication No. 2009/0127589; and U.S. Patent Publication No. 2009/0026082, which are incorporated by reference in their entireties.

In one aspect, the disclosed methods, compositions, systems, apparatuses and kits can be used for carrying out label-free nucleic acid sequencing, and in particular, ion-based nucleic acid sequencing. The concept of label-free detection of nucleotide incorporation has been described in the literature, including the following references that are incorporated by reference: Rothberg et al, U.S. patent publication 2009/0026082; Anderson et al, Sensors and Actuators B Chem., 129: 79-86 (2008); and Pourmand et al, Proc. Natl. Acad. Sci., 103: 6466-6470 (2006). Briefly, in nucleic acid sequencing applications, nucleotide incorporations are determined by measuring natural byproducts of polymerase-catalyzed extension reactions, including hydrogen ions, polyphosphates, PPi, and Pi (e.g., in the presence of pyrophosphatase). Examples of such ion-based nucleic acid sequencing methods and platforms include the Ion Torrent PGM™ or Proton™ sequencer (Ion Torrent™ Systems, Life Technologies Corporation).

In some embodiments, the disclosure relates generally to methods for sequencing nucleic acid templates. In one exemplary embodiment, the disclosure relates generally to a method for obtaining sequence information from polynucleotides, comprising: incorporating a terminator nucleotide at the extendible end of the nucleic acid template; and detecting a non-optical signal indicating the nucleotide incorporation using a sensor that detects by-products (e.g., cleavage products) from the nucleotide incorporation reaction. In some embodiments, methods for sequencing comprise: (a) providing a surface including one or more reaction sites containing a polymerase and a nucleic acid template that has, or is hybridized to, an extendible end; (b) performing a first nucleotide flow by contacting one or more of the reaction sites with a first solution including one or more types of terminator nucleotide; (c) incorporating at least one type of a terminator nucleotide at the extendible end of the nucleic acid template contained within at least one of the reaction sites using the polymerase; and (d) detecting a non-optical signal indicating the nucleotide incorporation using a sensor that is attached or operatively linked to the at least one reaction site. Optionally, the sensor comprises a FET sensor. Optionally, at least one reaction site includes one or more FET sensors. Optionally, the methods for sequencing further include: de-blocking the terminator nucleotide which is incorporated. Optionally, the methods for sequencing further include: performing a second nucleotide flow by contacting one or more of the reaction sites with a second solution including one or more types of nucleotides, where the second solution contains one or more terminator nucleotides, one or more non-terminator nucleotides, or a mixture of both. Optionally, the methods for sequencing further include: incorporating at least a second nucleotide, where the second nucleotide is a terminator nucleotide or non-terminator nucleotide from the second solution. Optionally, the methods for sequencing further include: detecting a second non-optical signal indicating the second incorporated nucleotide using the sensor that is attached or operatively linked to the at least one reaction site.

In some embodiments, the template-dependent synthesis includes incorporating one or more nucleotides in a template-dependent fashion into a newly synthesized nucleic acid strand.

Optionally, the methods can further include producing one or more ionic byproducts of such nucleotide incorporation.

In some embodiments, the methods can further include detecting the incorporation of the one or more nucleotides into the sequencing primer. Optionally, the detecting can include detecting the release of hydrogen ions.

In another embodiment, the disclosure relates generally to a method for sequencing a nucleic acid, comprising: disposing the nucleic acid templates into a plurality of reaction chambers, wherein one or more of the reaction chambers are in contact with a field effect transistor (FET). Optionally, the method further includes contacting the nucleic acid templates which are disposed into one of the reaction chambers, with a polymerase thereby synthesizing a new nucleic acid strand by sequentially incorporating one or more nucleotides (e.g., terminator nucleotides) into a nucleic acid molecule (e.g., extendible end). Optionally, the method further includes generating one or more hydrogen ions as a byproduct of such nucleotide incorporation. Optionally, the method further includes detecting the incorporation of the one or more nucleotides by detecting the generation of the one or more hydrogen ions using the FET.

In some embodiments, the detecting includes detecting a change in voltage and/or current at the at least one FET within the array in response to the generation of the one or more hydrogen ions.

In some embodiments, the FET can be selected from the group consisting of: ion-sensitive FET (isFET) and chemically-sensitive FET (chemFET).

In some embodiments, the disclosed methods for detecting nucleotide incorporation and/or performing nucleic acid sequencing allow sequencing of nucleic acid templates at accuracies not provided by current sequencing methods. For example, in some embodiments, the disclosed methods include sequencing a stretch of contiguous nucleotides within a nucleic acid template with an error rate of less than 0.1%. Optionally, the error rate is less than 0.001%. In some embodiments, the error rate includes a mismatch error rate of less than 0.001%, optionally less than 0.0001%. In some embodiments, the error rate includes an in/del error rate of less than 0.1%, optionally less than 0.01%.

In some embodiments, the disclosure relates generally to methods (and related compositions, systems, kits and apparatuses) for nucleic acid sequencing, comprising identifying a series of contiguous nucleotides in a nucleic acid template according to any of the methods disclosed herein.

In some embodiments, the disclosure relates generally to methods (and related compositions, systems, apparatuses and kits) for nucleic acid sequencing, comprising: providing a surface including one or more reaction sites that contain a nucleic acid template having, or hybridized to, an extendible end and a polymerase; extending the extendible end by serially incorporating a plurality of nucleotides at the extendible end of at least one nucleic acid template using a polymerase, where at least one of the incorporated nucleotides is a reversible terminator nucleotide, and wherein the extending includes deblocking any incorporated reversible terminator nucleotide prior to next incorporation of a succeeding nucleotide; detecting at least two successive nucleotide incorporations and determining the identities of at least two successively incorporated nucleotides at a total error rate of less than 0.1%. In some embodiments, the total error rate is less than 0.01%. Optionally, the total error rate includes a mismatch error rate of less than 0.001%, optionally less than 0.0001%. Optionally, the total error rate includes an in/del error rate of less than 0.1%, optionally less than 0.01%

In some embodiments, the disclosure relates generally to systems for performing nucleotide incorporation. The system optionally includes a flow cell containing a surface. The surface optionally includes one or more reaction sites containing a polymerase and a nucleic acid template. The nucleic acid template optionally has, or is hybridized to, an extendible end. The system can include an inlet having one end connected to the flow cell. The inlet can include another end connected to a one or more reservoirs containing one or more types of nucleotide. The nucleotide can be a terminator nucleotide. In some embodiments, the system further includes a sensor configured to detect a non-optical signal indicating a nucleotide incorporation occurring at least one of the reaction sites.

What is claimed is:

1. A method for performing nucleotide incorporation, comprising:
   a) providing a surface including one or more reaction sites, each site operatively linked to an ion-sensitive field effect transistor (ISFET), wherein one or more reaction sites contain a polymerase and a nucleic acid template that has, or is hybridized to, an extendible end;
   b) performing a first nucleotide flow of a first series of nucleotide flows at one or more reaction sites wherein in the first nucleotide flow the one or more reaction sites is contacted with a first solution containing one or more types of terminator nucleotides;
   c) incorporating a first terminator nucleotide at the extendible end contained within one or more reaction sites using the polymerase;
   d) detecting using the ISFET a non-optical signal indicating the nucleotide incorporation of the first terminator nucleotide;
   e) deblocking the first incorporated terminator nucleotide to generate a second extendible end;
   f) performing one or more subsequent nucleotide flows by contacting the one or more reaction sites with subsequent solutions containing one or more types of terminator nucleotides, thereby incorporating terminator nucleotides from the subsequent solutions and synthesizing an extension product which is annealed to the nucleic acid template, and after each subsequent nucleotide flow (i) detecting the presence or absence of a non-optical signal, and (ii) deblocking an incorporated subsequent terminator nucleotide to generate a subsequent extendible end, wherein steps (b)-(f) are conducted in the one or more reaction sites;
   g) identifying contiguous nucleotides in the nucleic acid template contained within the one or more reaction sites using for each template in the one or more reaction sites only the non-optical signals from that reaction site; and
   h) obtaining a first sequencing read from the extension product.

2. The method of claim 1, further including analyzing the non-optical signal from the first incorporated terminator nucleotide.

3. The method of claim 1, further including identifying the first incorporated terminator nucleotide.

4. The method of claim 1, wherein the deblocking includes removing a terminator moiety from the terminator nucleotide.

5. The method of claim 1, wherein the first and/or the subsequent solutions include only a single type of nucleotide.

6. The method of claim 1, wherein the subsequent solutions of the first series of nucleotide flows include a non-terminator nucleotide.

7. The method of claim 1, wherein the first series of nucleotide flows includes at least two flows containing one or more terminator nucleotides.

8. The method of claim 1, wherein the only nucleotides in all the flows in the first series of nucleotide flows are terminator nucleotides.

9. The method of claim 1, wherein the first series of nucleotide flows includes at least one flow containing a non-terminator nucleotide.

10. The method of claim 3, further including identifying the first incorporated terminator nucleotide with an error rate of less than 0.1%.

11. The method of claim 10, further including identifying the first incorporated terminator nucleotide with an error rate of less than 0.001%.

12. The method of claim 1, wherein the polymerase is not linked to the reaction site.

13. The method of claim 1, further comprising:
   i) denaturing the extension product from the nucleic acid template contained within the one or more reaction sites;

j) performing a second series of nucleotide flows by contacting the one or more reaction sites with subsequent solutions containing one or more types of non-terminator nucleotides, thereby incorporating the subsequent non-terminator nucleotides and synthesizing a second extension product which is annealed to the nucleic acid template, and after each subsequent nucleotide flow in the second series detecting the presence or absence of a non-optical signal wherein the presence of a non-optical signal indicates incorporation of a subsequent non-terminator nucleotide; and k) obtaining a second sequencing read from the second extension product, and aligning the first and second sequencing reads to reconstruct the sequence of the nucleic acid template.

14. The method of claim 13, wherein the first nucleotide flow and the one or more subsequent nucleotide flows of step (f) comprise the first series of nucleotide flows, and wherein the subsequent nucleotide flows of step (j) comprise the second series of nucleotide flows.

15. The method of claim 14, further including determining the identity and number of nucleotides incorporated following each nucleotide flow in the first series.

16. The method of claim 14, wherein the second series of nucleotide flows includes at least one flow containing a terminator nucleotide.

17. The method of claim 14, wherein the first series of nucleotide flows consists only of flows containing a terminator nucleotide and the second series of nucleotide flows consists only of flows containing a non-terminator nucleotide.

* * * * *